United States Patent
Bystrov et al.

(10) Patent No.: US 10,548,570 B2
(45) Date of Patent: Feb. 4, 2020

(54) MEDICAL IMAGE NAVIGATION SYSTEM

(71) Applicant: KONINKLIJKE PHILIPS N.V., Eindhoven (NL)

(72) Inventors: Daniel Bystrov, Hamburg (DE); Torbjoern Vik, Hamburg (DE); Astrid Ruth Franz, Hamburg (DE); Harald Sepp Heese, Hamburg (DE); Rafael Wiemker, Kisdorf (DE); Dominik Benjamin Kutra, Karlsruhe (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/081,623

(22) PCT Filed: Mar. 3, 2017

(86) PCT No.: PCT/EP2017/054981
§ 371 (c)(1),
(2) Date: Aug. 31, 2018

(87) PCT Pub. No.: WO2017/149107
PCT Pub. Date: Sep. 8, 2017

(65) Prior Publication Data
US 2019/0090849 A1    Mar. 28, 2019

(30) Foreign Application Priority Data
Mar. 3, 2016   (EP) ..................................... 16158485

(51) Int. Cl.
*G06F 19/00*       (2018.01)
*A61B 8/00*        (2006.01)
(Continued)

(52) U.S. Cl.
CPC .............. *A61B 8/466* (2013.01); *A61B 5/055* (2013.01); *A61B 6/037* (2013.01); *A61B 5/004* (2013.01);
(Continued)

(58) Field of Classification Search
CPC ..................................................... G06F 19/321
(Continued)

(56) References Cited

U.S. PATENT DOCUMENTS 9,053,565 B2    6/2015  Buelow et al.
2008/0155451 A1  6/2008  Lundstrom et al.
(Continued)

FOREIGN PATENT DOCUMENTS

WO    2011042833 A1    4/2011

OTHER PUBLICATIONS

Turlington, et al., "New Techniques for Efficient Sliding Thin-Slab Volume Visualization", IEEE Transactions on Medical Imaging, vol. 20, No. 8, Aug. 2001, pp. 823-835.
(Continued)

*Primary Examiner* — Thomas J Lett

(57) ABSTRACT

A system and a method are provided for enabling a user to interactively navigate through a set of slice images, the set of slice images jointly representing an image volume showing an anatomical structure of a patient. A user may be enabled to switch from a static viewing mode to a navigation mode based on navigation commands received from a user input device operable by the user. A display processor may be configured for, in the static viewing mode, generating an output image comprising one slice image of the set of slice images. The display processor may be configured for, in the navigation mode, replacing the said one slice image in the output image by a volume rendering of a slab of the image volume, the slab comprising more than one slice image. The
(Continued)

system and method thus selectively switch to volume rendering, namely during navigation, whereas in a static (i.e., non-navigation) viewing mode, a slice image is shown. Advantageously, the user may thus follow structures more accurately when navigate through a volume image, thereby more quickly and accurately identifying slice images of interest.

13 Claims, 9 Drawing Sheets

(51) Int. Cl.
*A61B 5/055* (2006.01)
*A61B 6/03* (2006.01)
*G16H 30/40* (2018.01)
*A61B 5/00* (2006.01)

(52) U.S. Cl.
CPC .............. *A61B 5/0035* (2013.01); *A61B 6/032* (2013.01); *G06F 19/00* (2013.01); *G16H 30/40* (2018.01)

(58) Field of Classification Search
USPC .......................................................... 345/433
See application file for complete search history.

(56) References Cited

U.S. PATENT DOCUMENTS

| | | | | |
|---|---|---|---|---|
| 2008/0155468 | A1* | 6/2008 | Rosander | G06F 19/321 715/810 |
| 2010/0131887 | A1* | 5/2010 | Salazar-Ferrer | G06F 3/0481 715/788 |
| 2011/0002515 | A1* | 1/2011 | Futami | G06F 19/321 382/128 |
| 2013/0326386 | A1* | 12/2013 | Vendrell | G06F 19/321 715/771 |

OTHER PUBLICATIONS

Anonymous: "Volume rendering", Wikipedia, Feb. 3, 2016, XP055292871, Retrieved from the Internet: URL:https://en.wikipedia.org/w/in,.dex.php? title=Volume_rendering&oldid=703112448 [retrieved on Aug. 2, 2016], 8 pages.

* cited by examiner

MEDICAL IMAGE NAVIGATION SYSTEM

This application is the U.S. National Phase application under 35 U.S.C. § 371 of International Application No. PCT/EP2017/054981, filed on Mar. 3, 2017, which claims the benefit of European Application Serial No. 16158485.9, filed Mar. 3, 2016. These applications are hereby incorporated by reference herein.

FIELD OF THE INVENTION

The invention relates to a system for, and a method of enabling a user to interactively navigate through a set of slice images. The invention further relates to a workstation and imaging apparatus comprising the system, and to a computer program product comprising instructions for causing a processor system to perform the method.

BACKGROUND OF THE INVENTION

Medical image acquisition techniques such as Computed Tomography (CT), Magnetic Resonance (MR), etc., may provide a set or stack of slice images which together represent an image volume showing an anatomical structure of a patient. Such an image volume may provide a three-dimensional (3D) view of anatomical structures such as blood vessels, nodules, lesions or airways. Navigating through the image volume is often desired by clinicians, including but not limited to radiologists, for, e.g., diagnosis of a disease in the anatomical structure. For enabling a user to navigate through the image volume, the image volume may be displayed to the user as individual slice images through which the user may sequentially scroll. As such, the image volume may be visualized to the user in a slice-by-slice manner. One or more slice images from the set of slice images may comprise a region that is of particular interest to the user. For example, the set of slice images may show a blood vessel, and one or more slice images of the image volume may show a bifurcation or stenosis of the blood vessel which may be of particular interest to a radiologist.

Although other visualization techniques are known as well for visualizing an image volume, such as volume rendering as described in, e.g., US 2012/306849 A1, clinicians are known to prefer the display of slice images for at least diagnostic purposes.

SUMMARY OF THE INVENTION

The inventors have recognized that the display of slice images is not always optimal for enabling a user to interactively navigate through the image volume.

It would be advantageous to have an improved system or method for enabling a user to interactively navigate through a set of slice images.

To better address this concern, a first aspect of the invention provides a system for enabling a user to interactively navigate through a set of slice images, the set of slice images jointly representing an image volume showing an anatomical structure of a patient, the system comprising:
  an image data interface configured for accessing the set of slice images;
  a user input interface configured for receiving navigation commands from a user input device operable by the user, wherein said receipt of the navigation commands causes the system to switch from a static viewing mode to a navigation mode;
  a display processor configured for:
    in the static viewing mode, generating an output image comprising one slice image of the set of slice images; and
    in the navigation mode, replacing the said one slice image in the output image by a volume rendering of a slab of the image volume.

The user input interface may be configured for enabling the user to provide forward or backward navigation commands in the navigation mode. The display processor may be configured for, in response to the forward or backward navigation commands, adjusting a size of the slab within a respective direction in the image volume. The above measures provide an image data interface configured for accessing a set of slice images. The set of slice images, which may be also referred to as a stack of images, may comprise cross-sectional images which may be acquired by various imaging modalities that produces an image in the form of a plane through the body with the structures cut across. Such imaging modalities may include CT and MRI, positron emission tomography, SPECT scanning, ultrasonography, etc. A difference between sequential positions of each slice in the set of slice images may be indicative of a distance between the slices in the image volume represented by the set of slice images.

The above measures further provide a user input interface for receiving navigation commands from a user input device operable by the user. The user may use the user input device, e.g. a computer mouse, to provide navigation commands. For example, the user may press a mouse button while operating the scroll wheel. The receipt of the navigation commands, such as the operation of the scroll wheel while the mouse button is pressed, causes the system to switch from a static viewing mode to a navigation mode. The system switches may mean that at least a processor, e.g., the display processor, switches mode.

The above measures further provide a display processor configured for, in the static viewing mode, generating an output image comprising one slice image of the set of slice images. In the static viewing mode, the output image may be displayed on a display to allow the user to view a desired one of the slice images. In the navigation mode, the user may navigate through the image volume, e.g., and move from a currently displayed slice image to another part of the image volume. The display processor is further configured for, in the navigation mode, replacing the slice image comprised in the output image by a volume rendering of a slab of the image volume. As such, in the navigation mode, the display processor may compute a volume rendering of a slab of the image volume and display the volume rendering of the slab, rather than individual slice images. Thereby, the previously displayed slice image is replaced in the output image by the computed volume rendering.

It is noted that a slice image may refer to a cross section of the image volume defined by a single plane while a slab may refer to a sub-volume of the image volume, e.g., as defined by two parallel planes intersecting the image volume. Such slice images may represent, e.g., transaxial data, or be obtained by way of multi-planar reformatting of an image volume while having zero or a limited thickness. In contrast, the thickness of the slab is non-zero and greater than that of the slice. Effectively, the slab may thus comprise the visual information of two or more slice images. As such, the volume rendering may be calculated based on two or more slice images of the set of slice images. The slice images comprised in the slab may be adjacent or distanced slice images in the set of slice images.

However, inventors have further recognized that, despite being not suitable for visualization, volume rendered images are suitable for navigation, e.g., because they are typically based on multiple slices and thus provide a larger field of view of the image volume and thereby enabling a user to 'look-ahead' during navigation. Such look-ahead may facilitate navigation, for example in that it may help a user to follow anatomical structures more accurately during the navigation. This may hold, for example, when the anatomical structures are perpendicular or diagonal to a viewing plane, when the anatomical structures have branches, etc. Hence, in accordance with the invention, the display processor automatically switches to volume rendering during navigation, whereas in a static viewing mode (i.e., non-navigation), the display processor reverts to showing a slice image. By switching from slice-by-slice viewing in a static viewing mode to volume rendering in a navigation mode, and back, the user may be advantageously enabled to view the slice images in-between navigation, while during navigation, the user is provided with additional visual information in the form of the volume rendering, with the additional visual information being provided by adjacent slice image. This additional visual information may advantageously help the user to more quickly and accurately identify relevant slice images during navigation.

In the navigation mode, the user may adjust the size of the slab using forward and backward navigation commands. This may result in more or less slice images being included in the slab which is volume rendered, thereby adjusting the depth provided by the volume rendering. For example, in response to forward navigation commands, the size of the slab may be increased in a particular direction, whereas in response to backward navigation commands, the size of the slab may be decreased again. Another example is that the forward navigation commands may increase the size of the slab in a particular direction, while the backward navigation commands may increase the size of the slab in the opposite direction. Such adjustment of size effectively represents a type of navigation through the image volume since different parts of the image volume are thereby included in the volume rendering.

In summary, the system and method as claimed shows 'original', i.e., non-volume rendered, slice images in the static viewing mode. However, as soon as the user starts navigating, the slice image is replaced by a volume rendering of the image volume and the user is thereby provided with additional visual information provided by adjacent slice images and not available in the static viewing mode. As such, the user may be advantageously enabled to follow structures more accurately when navigate through a volume image.

Optionally, the display processor is configured for further adjusting a location of the slab based on the navigation commands in the navigation mode. By adjusting size and/or location of the slab by way of navigation commands, the user is enabled to navigate through the image volume. For example, by including more slice images in the slab, the user may increase a depth provided by the volume rendering, and by adjusting a location of the slab, may effectively 'move' the slab through the image volume. Both adjustments, together and individually, have the effect that the user may visualize other parts of the image volume, thereby enabling the user to navigate through the image volume.

Optionally, the display processor is configured for, when exiting the navigation mode after a navigation from the one slice image to a destination slice image, generating an output image which comprises the destination slice image, and wherein the destination slice image is selected based on a current size and/or location of said volume rendered slab. The user is thus enabled to select a desired part of the image volume and thereby at least implicitly the destination slice image, as the destination slice image is selected based on the size/location of the volume rendered slab. It is noted that the volume rendered slab is the slab based on which the volume rendering is computed.

Optionally, the destination slice image is a middle or an outer slice image of the slab. By having a predetermined, i.e., 'fixed' selection of the destination slice image with respect to the slab, the user may quickly realize which slice image with respected to the slab is displayed in the static viewing mode immediately after the navigation.

Optionally, the display processor is configured to compute the volume rendering using a volume rendering technique selected from at least one of: maximum intensity projection, minimum intensity projection, shaded surface display, direct volume rendering, and virtual endoscopy. These techniques are suitable volume rendering techniques.

Optionally, the volume rendering is computed using a volume rendering technique which weights an influence of a contribution of image voxels of slice images comprised in the slab, and the influence is adjusted based on an image value indicated by a pointer on screen. A range of slices contributing to the volume rendering may be limited in order to remove contributions of slices that are further away from the current slice than a specified limit. In this way, far away structures may advantageously fade out when using large slabs, e.g., to navigate large distances throughout the set of slice images. By further adjusting the influence based on the image grey value indicated by a pointer on screen, the user is enabled to indicate, namely by way of suitably positioning the pointer on screen, which image grey value is considered to be relevant, e.g., representing a tissue of interest, and thus should have large influence in the volume rendering, and vice versa.

Optionally, the display processor is configured for, when computing the volume rendering, adjusting a contribution of each slice image comprised in the slab based on a distance between each respective slice image and the said one slice image of the set of slice images. Advantageously, the information provided by the slice images nearest to a current slice image may be emphasized when displayed to the user. Moreover, the volume rendering may be more similar to the slice image which may advantageously limit a switching effect when switching to navigation mode since. Limiting the switching effect may help the user to, e.g., more accurately compare the information provided by the current slice and the additional information provided in the slab by the added slices.

Optionally, the display processor is configured to generate a colored overlay on the volume rendering based on the contribution of each of the slice image comprised in the slab. This may assist the user to more easily and accurately distinguish between the information provided by slices closest to the slice of interest, which may help the user to visualize/analyze a slice of interest more accurately.

A workstation may comprise the system set forth.

An imaging apparatus may comprise the system set forth.

A further aspect of the invention provides a method of enabling a user to interactively navigate through a set of slice images, the set of slice images jointly representing an image volume showing an anatomical structure of a patient, the method comprising:

accessing the set of slice images;
receiving navigation commands from a user input device operable by the user,
in response to said receipt of the navigation commands, switching from a static viewing mode to a navigation mode;
in the static viewing mode, generating an output image comprising one slice image of the set of slice images; and
in the navigation mode, replacing the said one slice image in the output image by a volume rendering of a slab of the image volume.

The method may, but in unclaimed embodiments does not need to, further comprise:
enabling the user to provide forward or backward navigation commands in the navigation mode; and
in response to the forward or backward navigation commands, adjusting a size of the slab in a respective direction within the image volume.

A computer program product may comprise instructions for causing a processor system to perform the method set forth.

In an embodiment which is not within the scope of the claims as filed, a system may be provided which is in general configured for enabling a user to interactively navigate through a set of slice images, the set of slice images jointly representing an image volume showing an anatomical structure of a patient, the system comprising:
an image data interface configured for accessing the set of slice images;
a user input interface configured for receiving navigation commands from a user input device operable by the user, wherein said receipt of the navigation commands causes the system to switch from a static viewing mode to a navigation mode;
a display processor configured for:
in the static viewing mode, generating an output image comprising one slice image of the set of slice images; and
in the navigation mode, replacing the said one slice image in the output image by a volume rendering of a slab of the image volume.

In another embodiment which is not within the scope of the claims as filed, a corresponding method may be provided.

It will be appreciated by those skilled in the art that two or more of the above-mentioned embodiments, implementations, and/or aspects of the invention may be combined in any way deemed useful.

Modifications and variations of the image acquisition apparatus, the workstation, the method, and/or the computer program product, which correspond to the described modifications and variations of the system, can be carried out by a person skilled in the art on the basis of the present description.

A person skilled in the art will appreciate that the method may be applied to multi-dimensional image data, e.g. to three-dimensional (3-D) or four-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
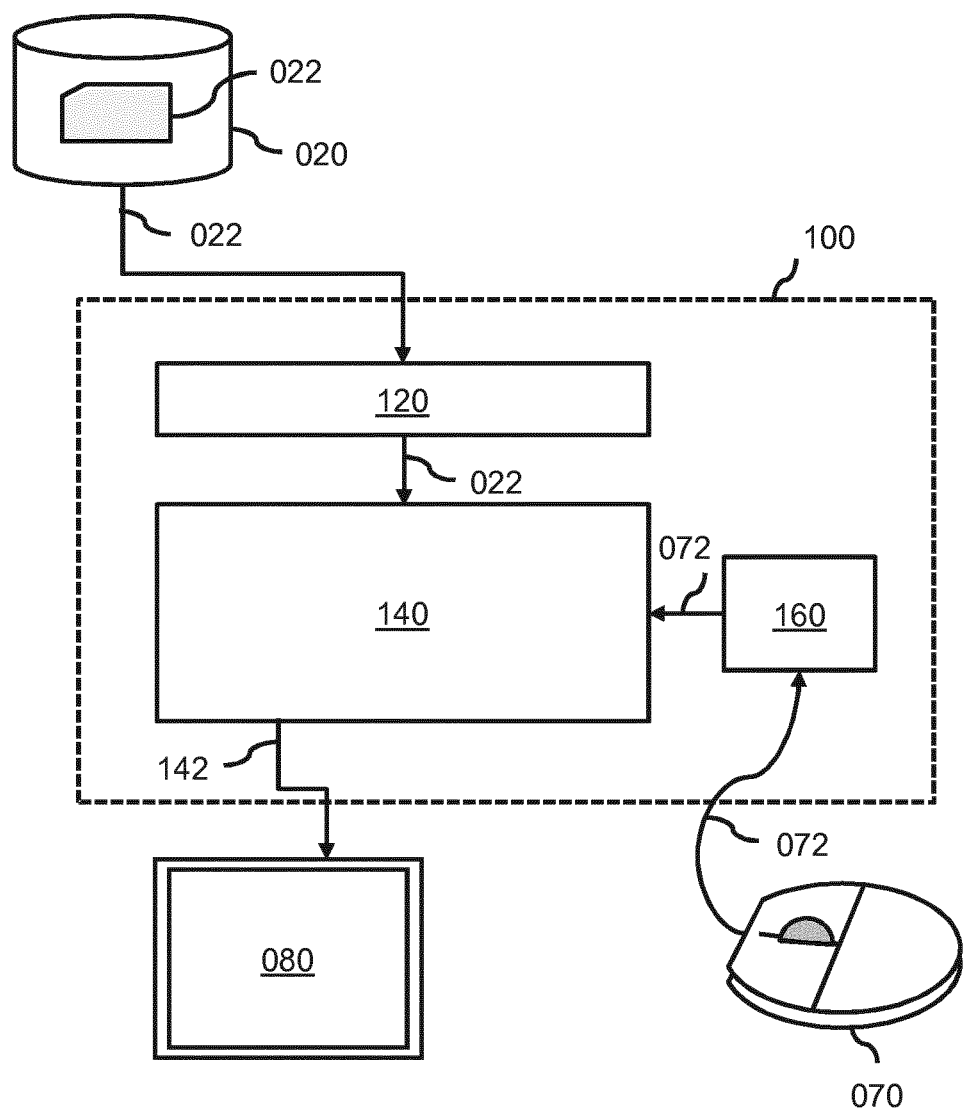
FIG. 1 shows a system for enabling a user to interactively navigate through a set of slice images representing an image volume showing an anatomical structure of a patient.

FIG. 1 shows a system 100 for enabling a user to interactively navigate through a set of slice images, with the set of slice images jointly representing an image volume showing an anatomical structure of a patient. The system 100 comprises an image data interface 120 configured for accessing the set of slice images. In the example of FIG. 1, the image data interface 120 is shown to be connected to an external image repository 020 which comprises the data 022 representing the set of slice images. For example, the image repository 020 may be constituted by, or be part of, a Picture Archiving and Communication System (PACS) of a Hospital Information System (HIS) to which the system 100 may be connected or comprised in. Accordingly, the system 100 may obtain access to the set of slice image data 022 via the HIS. Alternatively, the image data 022 may be accessed from an internal data storage of the system 100. In general, the image data interface 120 may take any suitable form, such as a network interface to a local or wide area network, e.g., the Internet, a storage interface to an internal or external data storage, etc.

The system 100 further comprises a user input interface 160 configured for receiving navigation commands from a user input device operable by the user, wherein said receipt of the navigation commands causes the system 100 to switch from a static viewing mode to a navigation mode. As such, the user input interface 160 may enable the user to switch from a static viewing mode to a navigation mode based on navigation commands received from a user input device 070 operable by the user. User input data 072 representing the navigation commands may be obtained from the user input device 070. It is noted that the user input device 070 may take various forms, including but not limited to a computer mouse 070, touch screen, keyboard, etc. The user input interface 160 may comprise an input interface 170 which may be of a type which corresponds to the type of user input device 070, i.e., it may be a thereto corresponding user device interface. The user input interface 160 may comprise a display output 180 for receiving output image 142 and for providing display data 082 to a display 080. The display may be any suitable display, such as, e.g., a computer monitor or television. The display data may, for example, comprise output image comprising one slice image of the set of slice images.

The system 100 further comprises a display processor 140. The display processor 140 is configured for, in the static viewing mode, generating the output image 142 comprising one slice image of the set of slice images. The display processor 140 is further configured for, in the navigation mode, replacing the said one slice image in the output image by a volume rendering of a slab of the image volume, the slab comprising more than one slice image. The display processor 140 of the example of FIG. 1 is shown to receive the slice image data 022 from the image input interface 120, to receive user input data 072 from the user input interface 160, and to output the output image 142.

The system 100 may be embodied as, or in, a single device or apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system, e.g., the display processor 140, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model.

Figure 2:
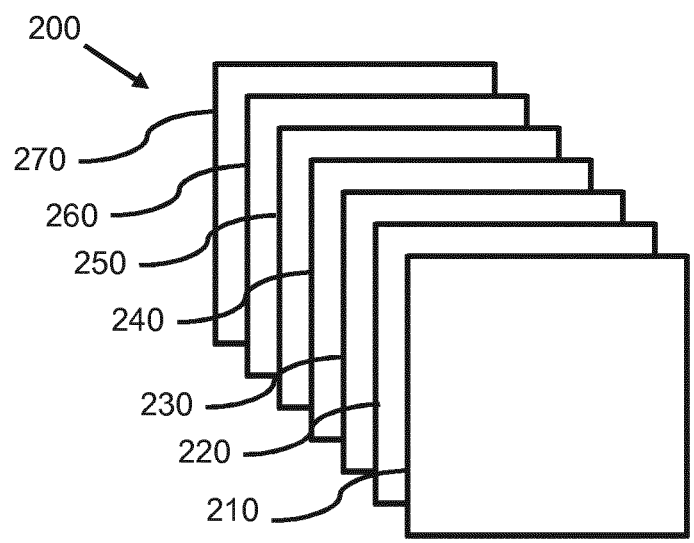
FIG. 2 shows a set of slice images representing an image volume.

FIG. 2 shows a set 200 of slice images 210-270 representing an image volume. The set 200 of slice images may be, e.g., a stack of slice images obtained by, e.g., CT, MRI modalities. The image volume may be a three-dimensional reconstruction of a human anatomical structure. The system 100 of FIG. 1 may receive the image data representing the set of slice images 210-270 and may generate an output image comprising a slice image of the set of slice images. The user may be enabled to view the single slice of the set of slice images in the display of FIG. 1, when the user selects the static viewing mode.

Figures 3A, 3B:
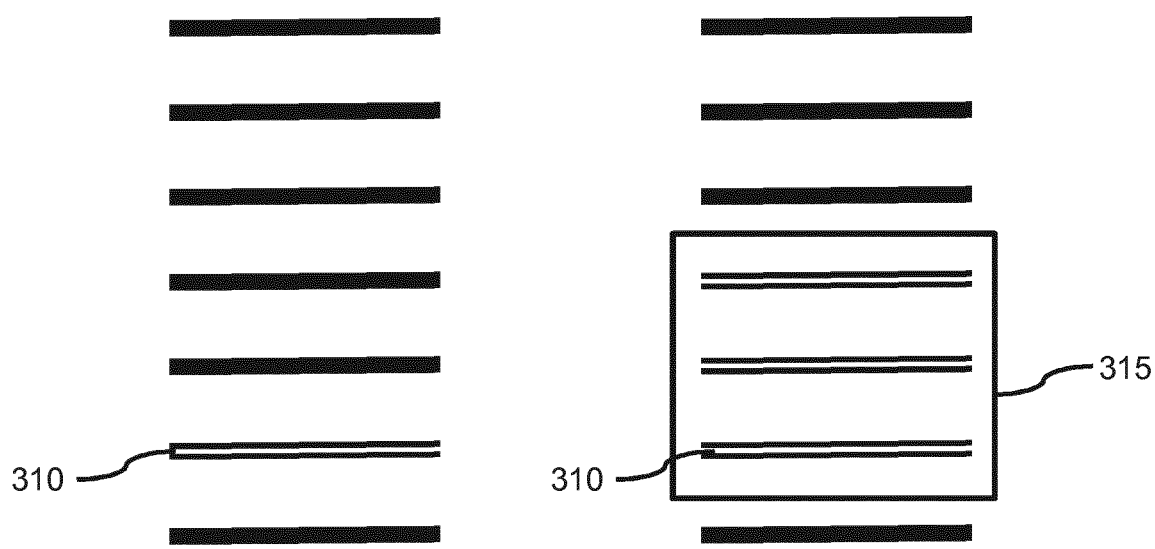
FIG. 3a shows an overhead view of the set of slice images of FIG. 2, wherein one of the slice images is being displayed to the user in a static viewing mode.
FIG. 3b shows a slab of the image volume which is volume rendered in a navigation mode, the slab comprising the previously displayed slice image.

FIG. 3a shows an overhead view of the set 200 of slice images of FIG. 2, wherein one of the slice images 310 is indicated as the image being displayed to the user in the static viewing mode. The system 100 of FIG. 1 may further enable the user to interactively navigate through the set 200 of slice images, when the user select a navigation mode of the system 100 instead of the static viewing mode. In the navigation mode, a volume rendering of a slab 315 of the image volume may be calculated and replace the said single slice 310 image in the output image. FIG. 3b shows the slab 315 of the image volume of FIG. 2 in a navigation mode. The slab 315 may encompass a plurality of slice images. The slab of FIG. 3b is shown to comprise the indicated slice image 310 of FIG. 3a and two more slice images adjacent to the indicated slice image. The volume rendering calculated from such a slab may provide a larger field of view of the image volume, e.g., being comprising a number of slice images, and thereby enable a user to follow anatomical structures which may be comprises in the image volume during a navigation.

It is further noted that volume rendering is a known in fields such as visualization and computer graphics. Volume rendering may be defined, in general, as a set of techniques used to display a 2D projection of a 3D discretely sampled data set, typically a 3D scalar field. The volume rendering may be computed based on various techniques such as maximum intensity projection, minimum intensity projection, shaded surface display, direct volume rendering, virtual endoscopy, etc. In a non-limiting example, a direct volume rendering may be used which may require every sample value to be mapped to opacity and a color. This may be done with a transfer function. Examples of such transfer functions may include a piecewise linear function, a simple ramp, an arbitrary table, etc. Once converted to an RGBA value, the composed RGBA result may be projected on corresponding pixel of a frame buffer. It is noted that RGBA stands for red, green, blue, alpha. In another non-limiting example, minimum intensity projection may be used. In minimum intensity projection only voxels with minimum intensity may be picked out and projected that fall in the way of parallel rays traced from a viewpoint to a plane of projection. In an example of the minimum intensity projection, for each XY coordinate only the pixel along the Z-axis with the highest Hounsfield number may be represented. As a result, in a single bi-dimensional image all dense structures in a given volume may be observed. Using such approach, it may be possible, for example, to find hyperdense structures in a volume, independently of their position.

It is further noted that, for allowing the navigation, the user device 070 of the system 100 of FIG. 1 may be a computer mouse comprising a scroll wheel. The scroll wheel is a mechanically rotatable device that may allow the user to navigate through the set of slice images. For example, rotating the scroll wheel forward may issue a 'next' or 'forward' command, and rotating the scroll wheel backward may issue a 'previous' or 'backward' command. The navigation, as such, may enable the user to move from one slice image to another slice images in the set of slice images. Backward or forward directions of the navigation through the set of slice images may enable the user to move towards or away from a particular slice image of interest and view slice images adjacent and far away from that particular slice image. Once such a navigation command has been received by the system, e.g., a forward scroll using the scroll wheel, the system may automatically switch to a volume rendering. It is noted that, navigation commands may be provided in various other ways, e.g., using different types of user input devices, and/or by differently interacting with a user input device.

It is further noted that user may be further allowed to drag a pointer on a screen using, for example, the computer mouse. In an example, when the user drags the pointer, the system 100 may be configured to allow the user to navigate through the set of images in the navigation mode, and as part thereof, automatically switch to a volume rendering. As soon as the user releases the pointer, the system 100 may be configured to exit the navigation mode and return back to the static viewing mode, thus showing to the user on the screen of the display one single slice image of the set of slice images.

Figure 4A:
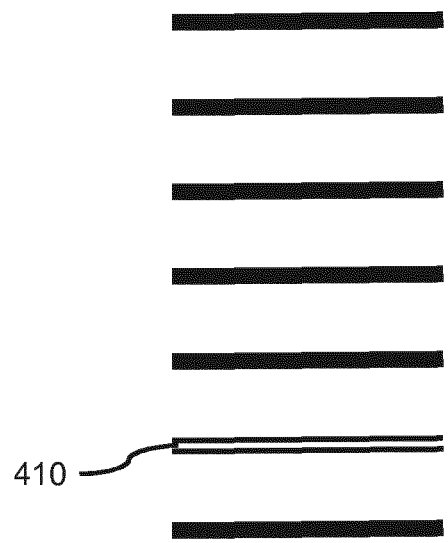
FIG. 4a shows the overhead view of the set of slice images of FIG. 2.
Figure 4B:
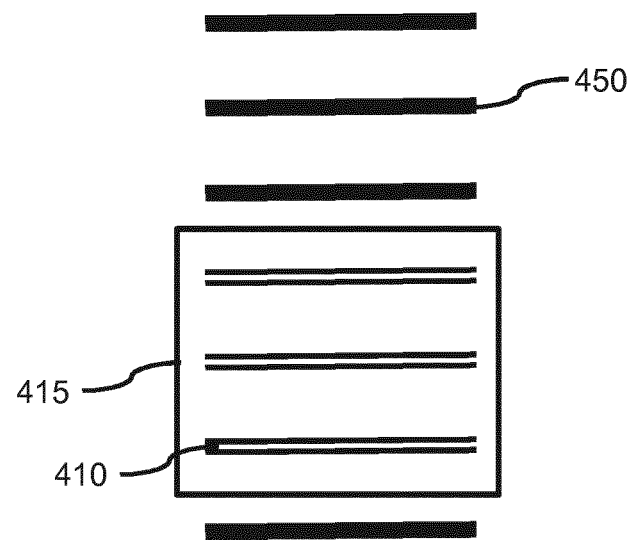
FIG. 4b shows another slab of the image volume during a navigation towards a destination slice image.
Figure 4C:
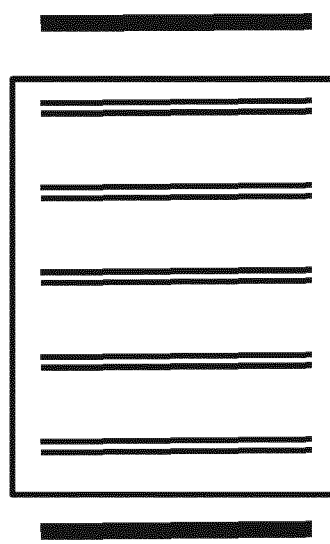
FIG. 4c shows a size of the slab of FIG. 4b being increased in response to navigation commands by adding slice images.
Figure 4D:
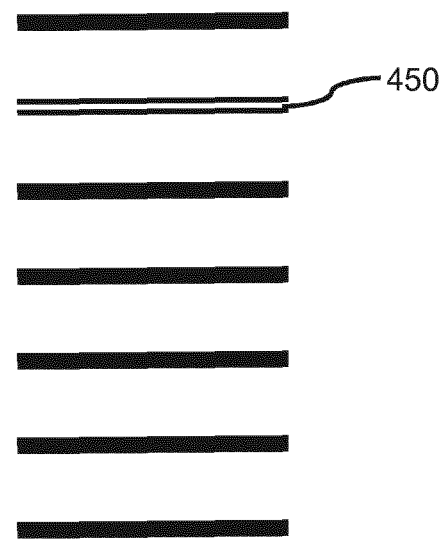
FIG. 4d shows the overhead view of the set of slice images, wherein the destination slice images is indicated as the image being displayed to the user in the static viewing mode after the navigation of FIG. 4c.

FIG. 4a shows the overhead view of the set 200 of slice images of FIG. 2, and FIG. 4b shows another 415 of the image volume during a navigation towards a destination slice image 450. The system 100 of FIG. 1 may enable the user to adjust a size of the slab by way of the navigation commands in the navigation mode. In the example of FIG. 4c, the user is shown to adjust the size of the slab 415. The slab 415 of FIG. 4a is shown to increase in size in FIG. 4c by adding slice images to the slab 415 for obtaining an enlarged slab 425. By increasing the size of the slab 415, the user may effectively navigate towards a desired destination slice image in that, by increasing the slab 415, the view of the image volume provided by the output image looks further 'ahead' in the image volume. Adjusting the size of the slab 415 may thus allow the user to access and view additional information of the image volume in the enlarged slab 425 provided by the added slice images. Using the provided information in the enlarged slab 425, the user may be enabled to obtain a more accurately visualization and follow structures when navigating through the image volume. Following the navigation, when the user switches back to static viewing mode, any slice image comprised in the slab 425 or at a vicinity of the slab 425 may be selected automatically or by the user and be displayed. FIG. 4d shows the overhead view of the set of slice images, wherein the destination slice images 450 is indicated as the image being displayed to the user in the static viewing mode after the navigation of FIG. 4c. It is noted that the destination slice image may be selected to be any slice image comprised in the slab, e.g., middle or an outer slice image of the slab, or it may be a slice image outside the current slab, e.g., it may be a slice image from an adjacent slab.

Figure 5A:
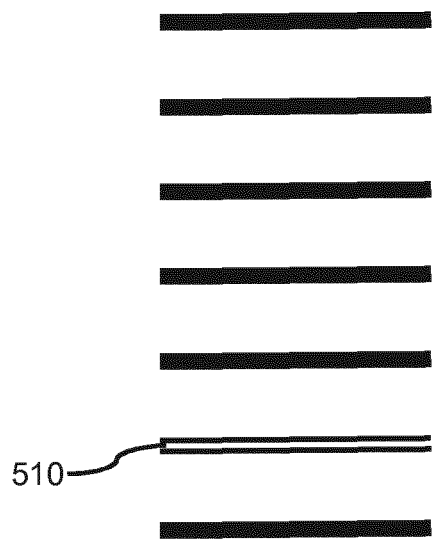
FIG. 5a shows the overhead view of the set of slice images of FIG. 2.
Figure 5B:
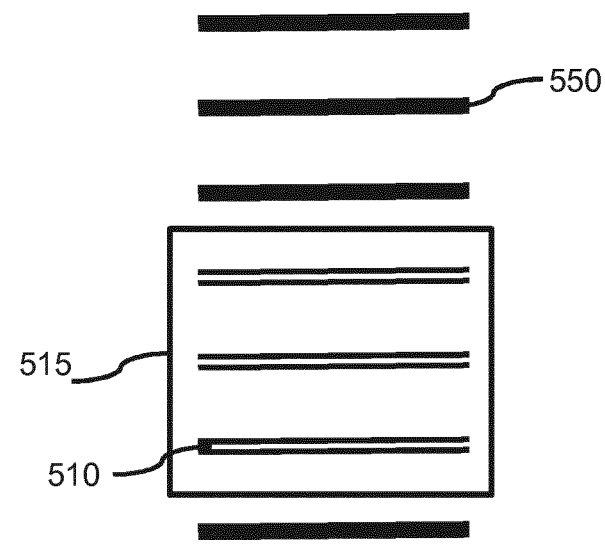
FIG. 5b shows the slab of the image volume which is volume rendered during a navigation towards a destination slice image.
Figure 5C:
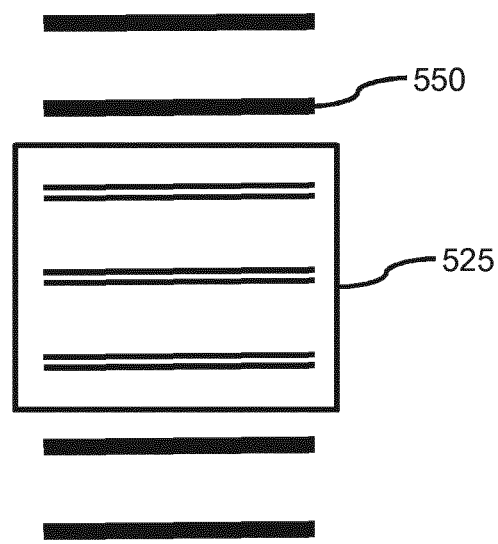
FIG. 5c shows the slab having been moved towards the destination slice image response to navigation commands in the navigation mode.
Figure 5D:
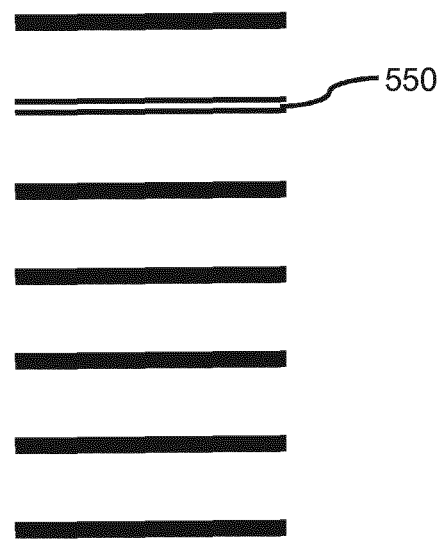
FIG. 5d shows the overhead view of the set of slice images, wherein the destination slice images is indicated as the image being displayed to the user in the static viewing mode after the navigation of FIG. 5c.

FIG. 5a shows the overhead view of the set 200 of slice images of FIG. 2, and FIG. 5b shows another slab 515 of the image volume during a navigation towards a destination slice image 550. The system 100 of FIG. 1 may enable the user to adjust a location of the slab 515 by way of the navigation commands in the navigation mode so that the user may be enabled to access and view further information. FIG. 5c shows a relocated slab 525 of which the location is adjusted, compared to slab 515 of FIG. 5b, towards the destination slice image 550. By displacing the slab 525 which may be towards or away from the destination slice image 550, the user may navigate back and forth through the image volume and select which slice images the user finds more desirable to be included in the slab 525 and thus in the volume rendering during the back and forth navigation. FIG. 5d shows the overhead view of the set of slice images, wherein the destination slice images 550 is indicated as the image being displayed to the user in the static viewing mode after the navigation of FIG. 5c.

Figure 6A:
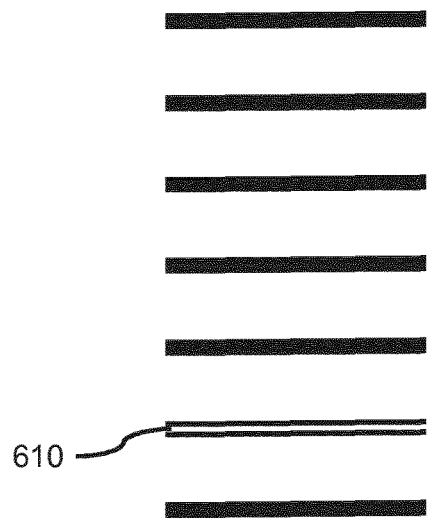
FIG. 6a shows the overhead view of the set of slice images of FIG. 2.
Figure 6B:
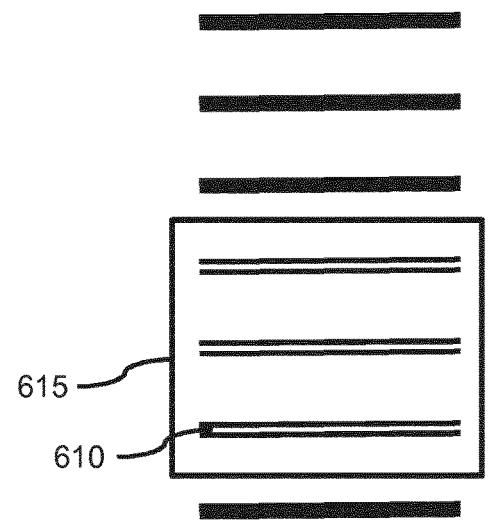
FIG. 6b shows another slab of the image volume during a navigation towards a destination slice image.
Figure 6C:
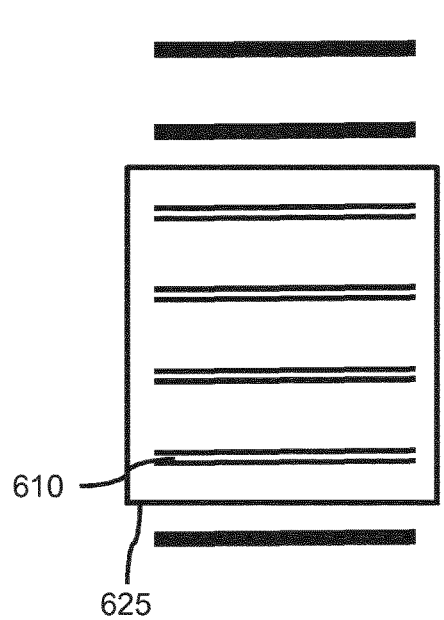
FIG. 6c shows a size of the slab of FIG. 6b being increased in response to navigation commands by adding slice images.
Figures 6D, 6E:
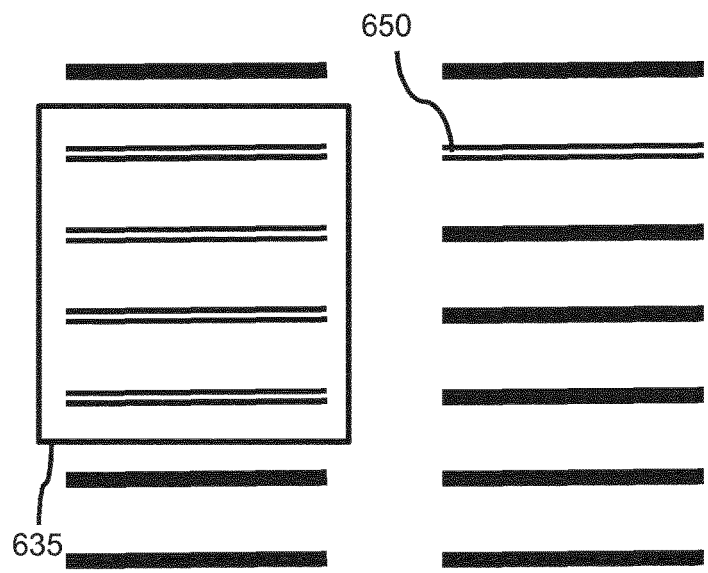
FIG. 6d shows a location of the slab of FIG. 6c having been adjusted towards the destination slice image.
FIG. 6e shows the overhead view of the set of slice images, wherein the destination slice images is indicated as the image being displayed to the user in the static viewing mode after the navigation of FIG. 6d.

FIG. 6a shows the overhead view of the set 200 of slice images of FIG. 2, and FIG. 6b shows another slab 615 of the image volume during a navigation towards a destination slice image 650. The system 100 of FIG. 1 may enable the user to adjust both size and location of the slab 615 by way of the navigation commands in the navigation mode. FIG. 6c shows a size of the slab 615 of FIG. 6b being increased in response to navigation commands by adding slice images to the slab 625. FIG. 6d shows a location of the slab 625 of FIG. 6c being adjusted towards the destination slice image 650. By adjusting both size and location of the slab 515, the user may obtain a flexible selection of the number and location of the slice images which are desired to be included in the volume rendering. FIG. 6e shows the overhead view of the set of slice images, wherein the destination slice images 650 is indicated as the image being displayed to the user in the static viewing mode after the navigation of FIG. 6d.

Figure 7:
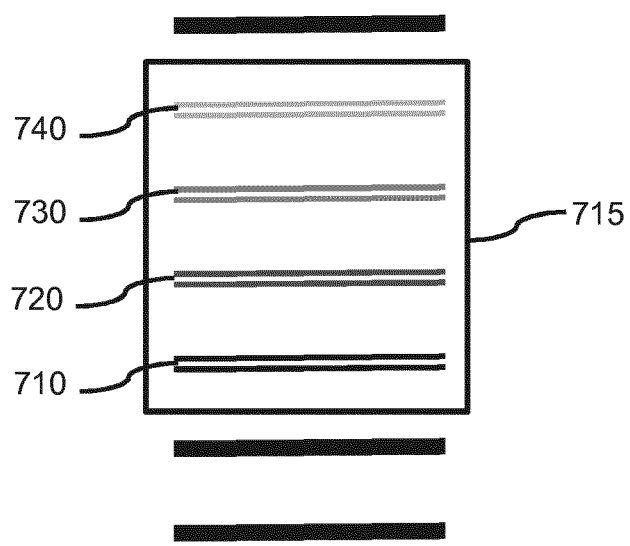
FIG. 7 shows another slab of the image volume during a navigation, wherein a contribution, represented by intensity, of each slice image comprised in the slab is adjusted based on the distance between each slice image and the first slice image of the slab.

FIG. 7 shows another slab 715 of the image volume during a navigation, wherein a contribution of each slice images 710-740 comprised in the slab 715 is adjusted based on the distance between each slice image and the first slice image 710 of the slab 715. In the example of FIG. 7, the contribution of each slice image 710-740 is shown to be represented as the intensity slice image. It is shown that when a slice image is closer to the first slice image 710 of the slab 715, the intensity of the slice image is greater. As such, the slice images 720-740 nearer to the first slice image 710 may be pronounced when being presented to the user and the user may focus more on the pronounced parts of the volume rendering. By focusing on the pronounced parts, the user may be enabled to follow structures more accurately and conveniently because a visual distraction of the user caused by less pronounced information may be reduced.

Figure 8:
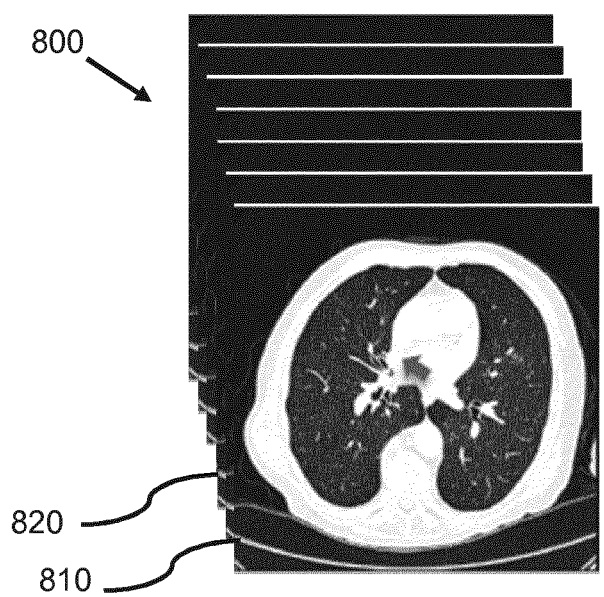
FIG. 8 shows a set of slice images jointly representing an image volume showing an anatomical structure of a patient.
Figure 9A:
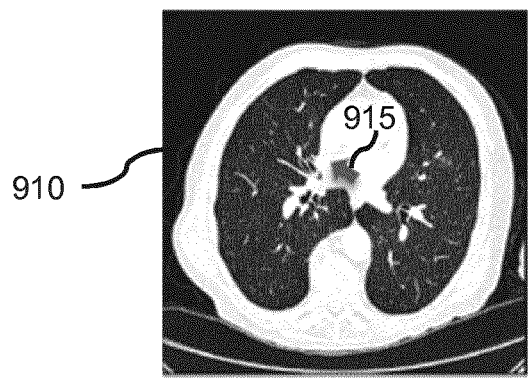
FIG. 9a shows a static view of a slice image of the set of slice images of FIG. 8 which may be displayed to a user.
Figure 9B:
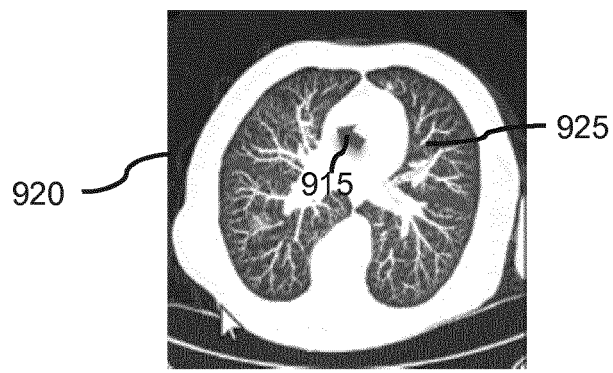
FIG. 9b shows a volume rendering of a slab of the image volume replacing the displaced slice image of FIG. 9a during a navigation.
Figure 9C:
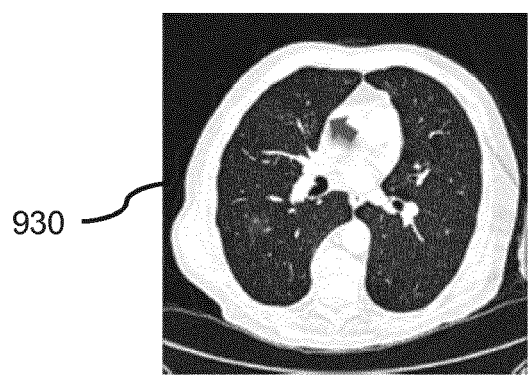
FIG. 9c shows another slice image of the set of slice images of FIG. 8 being displayed to the user after the navigation of FIG. 9b.

FIG. 8 shows a set 800 of slice images jointly representing an image volume showing an anatomical structure of a patient. A user may be enabled to visualize the slice image in a slice-by-slice manner in a static viewing mode. FIG. 9a shows a static view of a slice image 910 of the set 800 of slice images of FIG. 8 which may be displayed to a user. When the user wishes to follow the anatomical structure more accurately by navigating through the image volume, upon providing a navigation command by the user, a volume rendering of a sub-volume of the image volume, e.g. a slab may be calculated and automatically presented to the user instead of the slice image 910 of FIG. 9a. In this example, a pointer 915 is shown to be dragged on a screen by the user so as to provide the navigation command. FIG. 9b shows a volume rendering 920 of a slab of the image volume replacing the displayed slice image of FIG. 9*a* during a navigation. In FIG. 9*b*, the pointer of FIG. 9*a* is shown to be dragged and displaced by the user and thereby the navigation command may be provided to calculate, switch to the navigation mode and present the volume rendering to the user. In this example, the volume rendering may enable the user to, e.g., follow branches 925 of vessels in the anatomical structure more accurately. As soon as the user releases the pointer, an exit from the navigation mode may automatically occur and a slice image may be presented to the user. FIG. 9*c* shows another slice image 930 of the set 800 of slice images of FIG. 8 being displayed to the user after the navigation of FIG. 9*b*.

Figure 10:
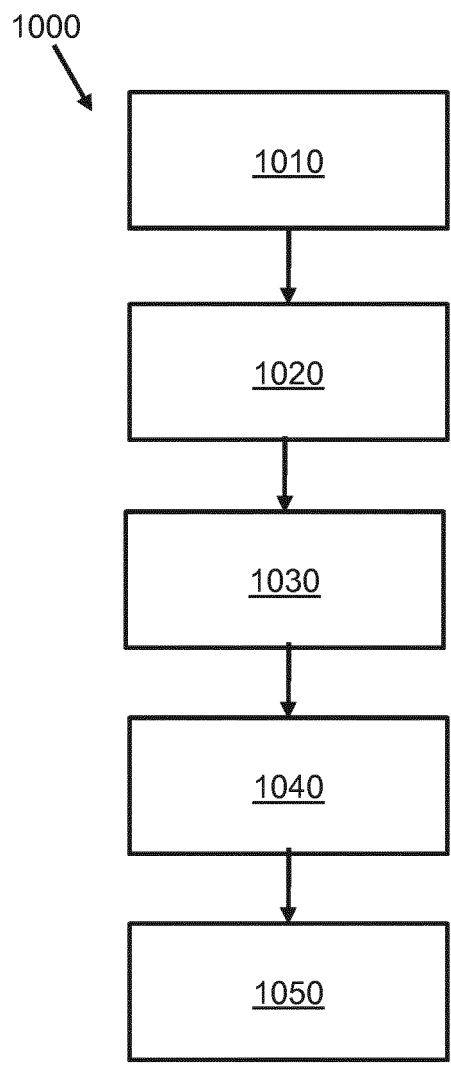
FIG. 10 shows a method of enabling a user to interactively navigate through a set of slice images, the set of slice images jointly representing an image volume showing an anatomical structure of a patient.

FIG. 10 shows a method 1000 of enabling a user to interactively navigate through a set of slice images, the set of slice images jointly representing an image volume showing an anatomical structure of a patient. The method 1000 comprises, in an operation titled "ACCESSING SLICE IMAGES", accessing 1010 the set of slice images. The method 1000 further comprises, in an operation titled "RECEIVING NAIGATION COMMANDS", receiving 1020 navigation commands from a user input device operable by the user. The method 1000 further comprises, in an operation titled "SWITCHING MODE", in response to said receipt of the navigation commands, switching 1030 from a static viewing mode to a navigation mode. The method 1000 further comprises, in an operation titled "GENERATING OUTPUT IMAGE", in the static viewing mode, generating 1040 an output image comprising one slice image of the set of slice images. The method 1000 further comprises, in an operation titled "UPDATING OUTPUT IMAGE", in the navigation mode, replacing 1050 the said one slice image in the output image by a volume rendering of a slab of the image volume, the slab comprising more than one slice image.

Figure 11:
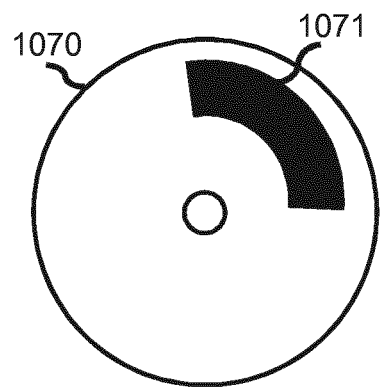
FIG. 11 shows a computer program product comprising instructions for causing a processor system to perform the method.

The method 1000 may be implemented on a computer as a computer implemented method, as dedicated hardware, or as a combination of both. As illustrated in FIG. 11, instructions for the computer, i.e., executable code, may be stored on a computer program product 1070, e.g., in the form of a series 1071 of machine readable physical marks and/or as a series of elements having different electrical, e.g., magnetic, or optical properties or values. The executable code may be stored in a transitory or non-transitory manner. Examples of computer program products include memory devices, optical storage devices 1070, integrated circuits, servers, online software, etc. FIG. 11 shows an optical disc.

According to the above and the abstract of the current application, system and a method are provided for enabling a user to interactively navigate through a set of slice images, the set of slice images jointly representing an image volume showing an anatomical structure of a patient. A user may be enabled to switch from a static viewing mode to a navigation mode based on navigation commands received from a user input device operable by the user. A display processor may be configured for, in the static viewing mode, generating an output image comprising one slice image of the set of slice images. The display processor may be configured for, in the navigation mode, replacing the said one slice image in the output image by a volume rendering of a slab of the image volume, the slab comprising more than one slice image. The system and method thus selectively switch to volume rendering, namely during navigation, whereas in a static (i.e., non-navigation) viewing mode, a slice image is shown. Advantageously, the user may thus follow structures more accurately when navigate through a volume image, thereby more quickly and accurately identifying slice images of interest.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for enabling a user to interactively navigate through a set of slice images, the set of slice images jointly representing an image volume showing an anatomical structure of a patient, the system comprising:
   an image data interface configured for accessing the set of slice images;
   a user input interface configured for receiving navigation commands from a user input device operable by the user, wherein said receipt of the navigation commands causes the system to switch from a static viewing mode to a navigation mode;
   a display processor configured for:
      in the static viewing mode, generating an output image comprising one slice image of the set of slice images; and
      in the navigation mode, replacing the said one slice image in the output image by a volume rendering of a slab of the image volume;
   wherein:
      the user input interface is configured for enabling the user to provide forward or backward navigation commands in the navigation mode; and
      the display processor is configured for, in response to the forward or backward navigation commands, adjusting a size of the slab within a respective direction in the image volume.

2. The system according to claim 1, wherein the display processor is configured for further adjusting a location of the slab based on the navigation commands in the navigation mode.

3. The system according to claim 1, wherein the display processor is configured for, when exiting the navigation mode after a navigation from the one slice image to a destination slice image, generating an output image which comprises the destination slice image, and wherein the destination slice image is selected based on a current size and/or location of said volume rendered slab.

4. The system according to claim 3, wherein the destination slice image is a middle or an outer slice image of the slab.

5. The system according to claim 1, wherein the display processor is configured to compute the volume rendering using a volume rendering technique selected from at least one of: maximum intensity projection, minimum intensity projection, shaded surface display, direct volume rendering, and virtual endoscopy.

6. The system according to claim 1, wherein the volume rendering is computed using a volume rendering technique which weights an influence of a contribution of image voxels of slice images comprised in the slab, and wherein the influence is adjusted based on an image value indicated by a pointer on screen.

7. The system according to claim 1, wherein the display processor is configured for, when computing the volume rendering, adjusting a contribution of each slice image comprised in the slab based on a distance between each respective slice image and the said one slice image of the set of slice images.

8. The system according to claim 7, wherein the display processor is configured to generate a colored overlay on the volume rendering based on the contribution of each of the slice image comprised in the slab.

9. The system according to claim 1, wherein the user input device is a computer mouse comprising a mouse button, and wherein the forward and backward navigation commands represent one of:
   operations of a scroll wheel of the computer mouse in a respective direction while the mouse button is pressed; or
   moving of an onscreen pointer in a respective direction using the computer mouse while the mouse button is pressed.

10. A workstation comprising the system according to claim 1.

11. An imaging apparatus comprising the system according to claim 1.

12. A method of enabling a user to interactively navigate through a set of slice images, the set of slice images jointly representing an image volume showing an anatomical structure of a patient, the method comprising:
    accessing the set of slice images;
    receiving navigation commands from a user input device operable by the user,
    in response to said receipt of the navigation commands, switching from a static viewing mode to a navigation mode;
    in the static viewing mode, generating an output image comprising one slice image of the set of slice images; and
    in the navigation mode, replacing the said one slice image in the output image by a volume rendering of a slab of the image volume;
    wherein the method further comprises:
       enabling the user to provide forward or backward navigation commands in the navigation mode; and
       in response to the forward or backward navigation commands, adjusting a size of the slab in a respective direction within the image volume.

13. A computer program product comprising instructions for causing a processor system to perform the method according to claim 12.

* * * * *